United States Patent [19]
Fawkes et al.

[11] Patent Number: 5,993,840
[45] Date of Patent: Nov. 30, 1999

[54] NON-WOVEN COMPOSITION WITH ANTIMICROBIAL PROTECTION AND USE THEREOF

[75] Inventors: David Melville Fawkes, Cheshire; John David Payne, Lancashire, both of United Kingdom

[73] Assignee: Zeneca Limited, London, United Kingdom

[21] Appl. No.: 09/011,255

[22] PCT Filed: Jun. 28, 1996

[86] PCT No.: PCT/GB96/01562

§ 371 Date: Jan. 29, 1998

§ 102(e) Date: Jan. 29, 1998

[87] PCT Pub. No.: WO97/05910

PCT Pub. Date: Feb. 20, 1997

[30] Foreign Application Priority Data

Aug. 3, 1995 [GB] United Kingdom ............... 9515896

[51] Int. Cl.$^6$ ..................................... A01N 25/34
[52] U.S. Cl. .................. 424/404; 424/405; 424/409; 424/414
[58] Field of Search ............................ 424/404, 405, 424/409, 414

[56] References Cited

FOREIGN PATENT DOCUMENTS 174 128  3/1986  European Pat. Off. .

*Primary Examiner*—S. Mark Clardy
*Assistant Examiner*—Kathryne E. Shelborne
*Attorney, Agent, or Firm*—Pillsbury Madison & Sutro LLP

[57] ABSTRACT

A composition comprising a cellulosic non-woven material containing a mixture of polymeric biguanides such as poly (hexamethylene biguanide) together with an anionic polymer such as a polyacrylic acid super-absorbent and the use of such composition in disposable articles such as nappies.

13 Claims, No Drawings

NON-WOVEN COMPOSITION WITH ANTIMICROBIAL PROTECTION AND USE THEREOF

This application is the national phase of international application PCT/GB96/01562 filed Jun. 28, 1996 which designated the U.S.

The present invention relates to a composition comprising a non-woven material treated with polymeric biguanides and an anionic polymer and the use of such composition in disposable articles such as nappies, incontinence pads and feminine hygiene packs.

EP 174,128 discloses a disposable article such as a nappy, incontinence pad or feminine hygiene pack which is formed from a non-woven material treated with a mixture of linear polymeric biguanides having different molecular weights. These biguanides inhibit microbial growth in the article during use and in the case of nappies, especially, the use of the non-woven material containing the polymeric biguanides is said to reduce odours and provide protection against nappy rash or ammonia dermatitis. The linear polymeric biguanides are also said to be particularly useful for treating the non-woven material, especially cellulosic non-woven material, which is used as an absorbent layer in disposable articles because of their broad spectrum of microbiological activity, low toxicity and ease of application. The linear polymeric biguanides are adsorbed strongly by the cellulosic non-woven material and are easily applied uniformly throughout such material.

It has been found that when the non-woven material containing the polymeric biguanides is wetted with urine, as occurs during use of a disposable article such as a nappy or incontinence pad, some of the polymeric biguanides are desorbed. This desorption of polymeric biguanides is generally less than 20% by weight of that applied and is believed to be primarily the lower molecular weight fractions of the mixture of polymeric biguanides applied. This can lead to concentration gradients of polymeric biguanides within the non-woven material whereby the antimicrobial protection conferred by the polymeric biguanides is reduced in some regions below an effective level. It is also possible that the polymeric biguanides which are desorbed by urine may be removed from the locus of the non-woven material and hence no longer available to inhibit microbial growth within such material.

It has also been found that the polymeric biguanides which are desorbed from the non-woven material on contact with urine can be retained within the non-woven material by including an anionic polymer in admixture with the non-woven material and that the presence of the anionic polymer has no significant detrimental effect on the microbiological efficacy of the polymeric biguanides.

Thus, according to the present invention there is provided a composition comprising a) a non-woven material containing a mixture of polymeric biguanides; and b) an anionic polymer.

The non-woven material is preferably fibrous and may be any material suitable for use as the absorbent layer in disposable articles such as nappies, incontinence pads and feminine hygiene packs. Preferably, the fibres of the fibrous material have an average diameter from 1 to 200μ and especially from 10 to 100μ. Generally, the fibres are at least 1 mm in length. The fibres may be wet- or dry-laid and are preferably dry-laid to form a highly fluffed absorbent layer.

Examples of fibrous non-woven material are cellulose, modified cellulose and rayon. Other suitable fibrous non-woven materials are hydrophobic fibres which are treated with a wetting agent. Examples of such hydrophobic fibres are polyolefins such as polyethylene and polypropylene, polyacrylamide, polyester such as polyethylene teraphthalate, polyamide, polystyrene and polyurethane.

The non-woven material is preferably cellulose and especially wood pulp fibre which is optionally chemically modified by chemically cross-linking with a $C_{2-8}$-dialdehyde to give an average water retention value of from 28 to 50% by weight. Preferred wood pulp fibres are these generally known as semi-chemical wood pulps and especially chemical wood pulps such as those obtainable from sulphite or Kraft processes.

The individual polymers of the mixture of polymeric biguanides contain at least one recurring unit having two biguanide groups of Formula (1)

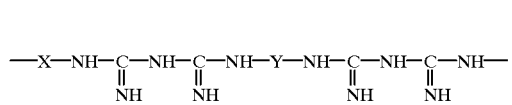
(1)

wherein X and Y may be the same or different and represent bridging groups in which together the total number of carbon atoms directly interposed between the pairs of nitrogen atoms linked by X and Y is from 9 to 17.

The bridging groups X and Y may be polymethylene chains, optionally incorporating hetero atoms, such as oxygen, sulphur or nitrogen, for example, ethylene oxyethylene, or cyclic nuclei which may be saturated or unsaturated, in which case the number of carbon atoms directly interposed between the pairs of nitrogen atoms linked by X and Y includes the shortest segment(s) of the cyclic group, or groups. Thus, for example, the number of carbon atoms directly interposed between the nitrogen atoms in the group

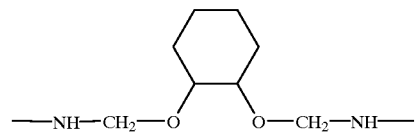

is 4 and not 8.

A preferred mixture of polymeric biguanides for use in the present invention is a mixture of poly(hexamethylene biguanides), in which X and Y both represent a —$(CH_2)_6$— group.

Polymeric biguanides may be prepared by the reaction of a bisdicyandiamide having the formula

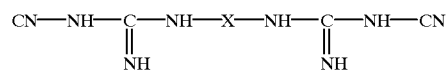

with a diamine $H_2N$—Y—$NH_2$, wherein X and Y have the meanings defined hereinbefore;

or by reaction between a diamine salt of dicyanamide having the formula

with a diamine $H_2N$—Y—$NH_2$ wherein X and Y have the meanings defined hereinbefore. These methods of preparation are described in GB 702,268 and GB 1,152,243 respectively, and any of the polymeric biguanides or mixtures described therein may be used in the present invention.

The biguanide polymer chains may be terminated either by an amino hydrochloride group or by an —NH—C(NH)—NH—CN group, and the terminating groups may be the same or different on each polymer chain.

Polymeric biguanides are generally obtained as mixtures in which the polymer chains are of different lengths and the number of individual biguanide units of formula 1 is from 1 to 40.

In the case of the preferred poly(hexamethylene biguanide) having the Formula (2)

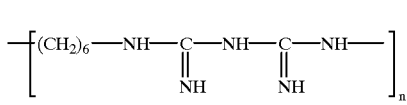

(2)

the value of n is from 2 to 40. The average molecular weight of the polymer mixture is preferably from about 1100 to about 3300.

The polymeric biguanides readily form water soluble salts with both inorganic and organic acids. The acid is preferably inorganic and especially hydrohalic such as hydrochloric acid.

Because the salts of polymeric biguanides are water soluble the mixture of polymeric biguanides are most easily handled in the form of aqueous concentrates and especially aqueous solutions of their salts. These concentrates preferably have a pH value of below 8 and especially below 7. Especially preferred aqueous solutions are those having a pH value below 4.5 as measured using an organic indicator. Preferably, the pH value of these aqueous concentrates is above 0.1, more preferably above 0.5 and especially above 1.0 as determined using an organic indicator. Concentrated aqueous solutions of this type are described in EP 485,079 and are commercially available as Vantocil IB and Cosmocil CQ (both Zeneca Ltd).

The anionic polymer is preferably substantially insoluble in urine so that it will not to any substantial extent dissolve and redistribute itself in the non-woven material during use and thereby form salts with the polymeric biguanides which impair the microbiological activity of the polymeric biguanides.

The solubility of the anionic polymer in urine is preferably not greater than 2%, more preferably not greater than 1%, even more preferably not greater than 0.5% and especially not greater than 0.1% by weight under the conditions of use of the non-woven material.

The anionic polymer is preferably obtainable by polymerising an anionic monomer or its anhydride or copolymerising an anionic monomer or its anhydride with non-ionic monomers. Preferred anionic monomers or anhydrides are olefinically unsaturated acids and anhydrides which contain at least one olefinic double bond and especially monomers having a single olefinic double bond. The anionic monomer may contain more than one anionic group but preferably contains only one anionic group.

The anionic group may be a phosphonic, phosphoric, sulphonic and especially a carboxylic acid group.

Examples of suitable anionic monomers are vinyl-phosphonic acid, styrene-phosphonic acid, 2-acrylamidopropanephosphonic acid, ethylidene-1,1-diphosphonic acid, hydroxyethylacrylate monophosphate, styrene sulphonic acid, 2-acrylamido-2-methylpropane sulphonic acid, sulphoethyl methacrylate, vinylsulphonic acid, methallyl sulphonic acid, propene sulphonic acid and particularly methacrylic acid and especially acrylic acid.

Preferred non-ionic monomers are of Formula (3)

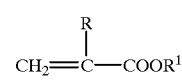

(3)

wherein
R is hydrogen or $C_{1-4}$-alkyl; and
$R^1$ is optionally substituted $C_{1-20}$-alkyl, aryl or $C_{5-14}$-cycloalkyl.

When R is alkyl it is preferably methyl.
When $R^1$ is alkyl it may be linear or branched and is preferably $C_{1-6}$-alkyl.
When $R^1$ is aryl it is preferably phenyl.
When $R^1$ is cycloalkyl it is preferably $C_{6-10}$-cycloalkyl such as cyclohexyl.
When $R^1$ is substituted $C_{1-20}$-alkyl, the substituent is preferably hydroxy or an acyloxy (i.e. alkylcarbonyloxy) group which may itself be substituted, for example, by an alkylcarbonyl group as in an acetoacetoxyethyl group.

Examples of non-ionic monomers are methyl (meth) acrylate, butyl (meth)acrylate, ethyl(meth)acrylate, 2-ethylhexyl(meth)acrylate, 2-hydroxyethyl(meth)acrylate and acetoacetoxyethyl(meth)acrylate.

Preferred anionic polymers are polyacrylic acid and copolymers of acrylic acid with one or more non-ionic monomers, poly(maleic acid) and copolymers of maleic acid with one or more non-ionic monomers, alginic acid, graft polymers of acrylic acid onto starch and carboxymethyl cellulose. Polyacrylic acid and its copolymers are optionally cross-linked and the MW range is generally from 1000 to 5,000,000. These acrylic acid based polymers may be derivable from a water-soluble polyacrylic acid which is cross-linked with, for example, trimethylolpropanetriacrylate, poly (allyl sucrose) or poly (allyl pentaerythritol). Especially preferred are the acrylic acid based polymers which act as fluid absorbing agents and are generally referred to as "super absorbents". Super absorbents based on polyacrylates and related polymers are described in, for example, EP 311,344 and Chemistry in Britain, 1994, pp 652–656 (F. L. Buchholz) and the disclosures and references in these two documents are incorporated herein by reference.

Poly(maleic acid) and its polymaleate derivatives may also be optionally cross-linked and typically have a MW in the range 1,000 to 5,000,000. Examples of polymers of this type are poly(vinyl ether-maleic acid), poly (methylvinylether-maleic acid) and poly(styrene-maleic acid).

Other useful anionic polymers are those derivable from cellulose such as carboxymethylcellulose, partially oxidised cellulose, sulphoethyl cellulose and phosphorylated cellulose.

The anionic polymer may be present in the free-acid form or in the form of a salt with an amine or a metal where the amine or metal cation is replaceable with any desorbed polymeric biguanide. Examples of suitable metals are lithium, potassium and particularly sodium. It is preferred, however, that at least some of the anionic groups of the anionic polymer are in the free-acid form. This is particularly the case where the anionic polymer is a super absorbent and it is preferred that at least 25 mole % and especially at least 50 mole % of the monomer units containing an anionic group which are used to make the anionic polymer are in the form of a salt. It is also preferred that at least 5 mole %, more preferably at least 10 mole % and especially at least 20 mole % of the monomers containing an anionic group which are used to make the anionic polymer are in the form of a free acid.

The anionic polymer may be in the form of sheets but is preferably present in the form of discrete particles or particle agglomerates. These particles can be of any shape such as spherical, semi-spherical, cubic, rod-like, needles or flakes and are preferably between 30μ and 2 mm as the weighted average of the smallest dimension of the individual particles.

The amount of anionic polymer relative to the non-woven material treated with a mixture of polymeric biguanides is dependent on the end use of the composition. Thus, in the case of disposable articles such as nappies and incontinence pads, the amount of anionic polymer may be just sufficient to prevent any desorbed polymeric biguanide escaping from the disposable article during use. However, when the anionic polymeric is also present as a super absorbent the amount of anionic polymer to non-woven material may be much higher. When the anionic polymer is a super absorbent the amount of anionic polymer is preferably at least 0.5%, more preferably at least 1% and especially at least 5% by weight relative to the total weight of anionic polymer and non-woven material. It is also preferred that the amount of anionic polymer is less than 50%, more preferably less than 30% and especially less than 20% by weight relative to the total weight of anionic polymer and non-woven material.

When the anionic polymer and non-woven material are used as the absorbent layer in a disposable article such as a nappy or incontinence pad such layer can be formed by any method known to the art and especially by processes that produce a web of anionic polymer in admixture with non-woven fibres. Preferably, the web is dry-laid, especially by air-laying.

According to a further aspect of the invention there is provided a process for forming an absorbent layer for use in a disposable article which comprises adding an anionic polymer to non-woven fibres containing a mixture of polymeric biguanides.

The mixture of polymeric biguanides may be applied to the non-woven material as an aqueous solution by any method known to the art such as spraying, dipping, padding, or substantive exhaustion processes. The pH of the aqueous solution of polymeric biguanide is preferably from 5 to 8 and especially from 6 to 7. When the polymeric biguanides are applied by exhaust or substantive exhaustion techniques, heating is not required because of their high substantivity for non-woven materials such as cellulosic material. The amount of polymeric biguanide is preferably at least 100, more preferably at least 500, and especially at least 1000 ppm relative to the non-woven material. It is also preferred that the amount of polymeric biguanide is not greater than 10,000, more preferably not greater than 8,000 and especially not greater than 6,000 ppm relative to the non-woven material.

As disclosed in EP 174,128, the polymeric biguanides which are used in component (a) of the present composition exhibit advantage over the bis-biguanides such as chlorohexidine especially in respect of a lower degree of foaming of their aqueous solution and broader spectrum of microbiological activity. Furthermore, the polymeric biguanides also exhibit higher substantivity for non-woven material, especially cellulosic non-woven material, and lower amounts of polymeric biguanides are desorbed from the non-woven material in the presence of urine. Non-woven material containing polymeric biguanide exhibit advantage over non-woven material containing a bis-biguanide such as chlorohexidine when the non-woven material is admixed with an anionic polymer especially in respect of microbiological activity.

The polymeric biguanides may be the only microbiologically active compounds present in the non-woven material or they may be present in conjunction with other microbiologically active compounds especially where it is desirable to broaden the spectrum of antimicrobial activity. Such other compounds must be substantially non-toxic and non-irritating in skin contact when the composition is used as an absorbent layer in disposable articles such as nappies, incontinence pads and feminine hygiene packs. Examples of such other microbiologically active compounds are quaternary ammonium compounds, especially halides, alkyl pyridinium compounds, especially halides, and simple bis-biguanides such as 1,6-bis(4-chlorophenyl)diguanide hexane (chlorohexidine) 1,6-bis(2-ethylhexyl) diguanide hexane (alexidine).

The composition may also contain other adjuvants for reducing or masking odours. Examples of such adjuvants are fragrances and organic acids. Preferred organic acids are those containing two or more carboxylic acid groups and especially those possessing a buffering capacity. The organic acid must not possess such a low pH value that it causes significant absorption of the mixture of polymeric biguanides from the non-woven materials. Consequently, preferred organic acids do not possess a pK value below 1. Particularly useful organic acids have a MW below 300 and especially below 200. Citric acid is especially preferred.

As noted hereinbefore, the composition of the present invention can be used as the absorbent layer in disposable articles such as nappies, incontinence pads and feminine hygiene packs. This absorbent layer is principally used for the collection and retention of body fluids such as urine and to reduce the generation of odours and incidence of skin rashes caused by the microbiological degradation of the body fluids.

According to a further aspect of the invention there is provided the use of the composition according to the invention for the collection of body fluids.

According to a still further aspect of the invention there is provided a disposable article containing the composition according to the present invention.

The invention is further illustrated by the following examples wherein all references are to parts by weight, unless expressed to the contrary.

EXAMPLES 1 AND 2

A chemical fluffed wood pulp as used in an infant's disposable nappy (10 parts) was stirred in water (100 parts) containing poly(hexamethylene biguanide) hydrochloride (hereinafter PHMB) (0.02 parts) at pH 6–7 for 10 mins at 20° C. The PHMB was totally exhausted onto the pulp which was then squeezed and dried to give a pulp containing 2000 ppm PHMB.

A sample of pulp was similarly treated to give 4000 ppm PHMB.

Mini-pads were also prepared by mixing aliquots of PHMB-containing pulp with a cross-linked polyacrylate super absorbent resin in the ratio of 85:15 pulp to resin.

Samples of the treated pulp and pads, respectively, (0.3 parts) were wetted with synthetic urine solutions (3 mls) and incubated at 37° C. for 24 hours. The composition of the synthetic urine in parts/liter was urea (20), uric acid (0.4), creatinine (0.67), hippuric acid (0.47), glycine (2.0), glucose (0.15), sodium chloride (10), disodium hydrogen phosphate (1.85), potassium sulphate (4.46), calcium chloride (0.36), magnesium chloride (0.28) and ferric chloride (trace).

After incubation, the samples were removed, filtered through a millipore filter and the PHMB content of the samples determined by colorimetric means using Eosin as indicator. The results are given in Table 1 below for duplicate samples which show that PHMB which is desorbed from the chemical pulp on treatment with synthetic urine is retained by the polyacrylate super absorbent. The detection limit for PHMB using this Eosin colorimetric method is about 10 ppm and hence a value <10 ppm represents no PHMB detected. Since the PHMB containing pulp and pads were suspended in synthetic urine at a liquor ratio of 10:1 the amount of PHMB desorbed from pulp containing 2000 ppm PHMB is about 18% (w/w) of that applied and about 22.5% (w/w) at the 4000 ppm PHMB level.

TABLE 1

| Example | Initial conc. of PHMB (ppm) | Conc. of desorbed PHMB in urine (ppm) CP | CP (85) + SAP(15) |
|---|---|---|---|
| 1 | 2000 | 40 | <10 |
|   |      | 32 | <10 |
| 2 | 4000 | 86 | 8 |
|   |      | 94 | 12 |
| Control |  | <10 | <10 |
|   |      | <10 | <10 |

Footnote to Table 1
Control is no PHMB
CP is chemical wood pulp
SAP is super absorbent polyacrylate.

EXAMPLE 3

The ability of the chemical fluffed wood pulp admixed with super absorbent polyacrylate resin to inhibit microbial growth was determined by subjecting the mini-pads described in examples 1 and 2 to a bacterial and yeast inoculum cultured in synthetic urine.

The synthetic urine was prepared according to the following recipe.

| Stock Solution | 8.77 parts | Sodium chloride |
|---|---|---|
|  | 3.48 parts | Dipotassium hydrogen phosphate |
|  | 1.56 parts | Sodium dihydrogen phosphate |
|  | 2.67 parts | Ammonium chloride |
|  | 6.44 parts | Sodium sulphate 10H$_2$O |
|  | 0.45 parts | 85–90% lactic acid |
|  | 4.00 parts | Yeast extract (Difco) |
|  | to 1,000 ml | Distilled water |

This stock solution was sterilised by autoclaving at 121° C. for 30 minutes.

| Urea-Glucose Solution | 36 parts | Urea |
|---|---|---|
|  | 0.18 parts | D-Glucose |
|  | to 100 ml | Distilled water |

The urea-glucose solution was sterilised by filtrated through a 0.22 μm Millipore filter.

| Salt Solution | 1.22 parts | Magnesium chloride 6H$_2$O |
|---|---|---|
|  | 0.88 parts | Calcium Chloride 2H$_2$O |
|  | to 20 ml | Distilled water |

The salt solution was sterilised by autoclaving at 121° C. for 30 minutes. All solutions were stored at +4° C. until required, then mixed in the ratio:

| Stock Solution | 94 ml |
|---|---|
| Urea-Glucose Solution | 5 ml |
| Salt Solution | 1 ml |

The synthetic urine was used immediately after mixing.

Three bacteria and one yeast were used in the present evaluation and were identified as follows:
Escherichia coli
Enterococcus faecalis
Proteus mirabilis
Candida albicans Each of the four organisms were cultured onto appropriate agar for 3 generations. 10 ml aliquots of sterile synthetic urine were inoculated separately with one colony of each organism, and incubated overnight at 37° C. The population of each was counted by haemocytometer and diluted in sterile synthetic urine to give $1 \times 10^4$ CFU/ml (CFU is colony forming units). The 3 bacteria were combined to give a mixed inoculum, whereas the yeast was used separately.

1 g incontinence pads were inoculated with 10 ml of either bacterial or yeast inoculum in a wide mouth, screw top glass jar, and incubated at 35° C. for 0, 5, 10 and 15 hours. Uninoculated pads were also incubated overnight to check for background contamination. Incubation was terminated by the addition of 100 ml sterile neutraliser (0.3% azolectin and 2% Tween 80) and vigorous shaking for 1 minute. Viable counts were determined by a serial dilution pour plate technique on tryptone glucose extract agar for the bacteria and malt extract agar for the yeast.

The pH of the synthetic urine after incubation was measured by aseptically transferring a drop of urine from the pad onto pH indicator paper, and estimating pH from the colour produced.

Odour was assessed by opening the glass jar and carefully sniffing the contents of the jar.

The results are recorded in the following Table 2 (bacteria) and Table 3 (yeast), respectively.

These results show that the bacteria grew strongly in the urine on untreated pads (control) from the initial inoculum of $10^4$ CFU/ml to about $10^9$ CFU/ml after 10 hours incubation. An ammoniacal odour became increasingly detectable after 10 hrs with a concurrent increase in pH clearly apparent after 15 hours incubation. Similarly, the yeast also grew strongly in the urine on the untreated pads (control) but at a slightly slower rate than the bacteria but with no detected odour or pH increase even after 15 hours incubation.

On pads containing PHMB, the growth of bacteria was considerably inhibited (Table 2) particularly over the initial 5 hour period where bacterial growth was reduced by three orders of magnitude for pads containing 2000 ppm and 4000 ppm PHMB, respectively, compared with the untreated control After 10 hours incubation, the pad containing 2000 ppm was exhibiting 2 orders of magnitude reduction in bacterial growth whereas the reduction was still 3 orders of magnitude at the 4000 ppm PHMB level. At the higher level of PHMB, bacteria growth was still suppressed after 15 hours incubation.

No increase in pH or development of odour caused by bacterial degradation of the urine was detected even after 15 hours incubation.

The growth of yeast (Table 3) was similarly inhibited by the PHMB treated pads compared with the control containing no PHMB.

When these results are combined with those from Examples 1 and 2 it is clear that PHMB which is desorbed from the cellulosic pulp upon contact with urine can be retained in the pad by the super absorbent polyacrylate resin and that a high level of inhibition of microbiological growth by PHMB is manifest.

TABLE 2

| Example | PHMB Conc. on Chemical Pulp (ppm) | | Bacterial Growth after time (hours) | | | |
|---|---|---|---|---|---|---|
| | | | 0 | 5 | 10 | 15 |
| Control | 0 | Count (CFU/ml) | $6.7 \times 10^3$ | $1.7 \times 10^7$ | $2.7 \times 10^9$ | $3.6 \times 10^9$ |
| | | pH | 7 | 7 | 7 | 8–9 |
| | | Odour | None | None | Slight | Strong |
| 3 | 2000 | Count (CFU/ml) | $6 \times 10^3$ | $7 \times 10^4$ | $3.8 \times 10^7$ | $1.5 \times 10^9$ |
| | | pH | 7 | 7 | 7 | 7 |
| | | Odour | None | None | None | Slight |
| 4 | 4000 | Count (CFU/ml) | $2 \times 10^3$ | $1 \times 10^4$ | $5 \times 10^6$ | $2.7 \times 10^7$ |
| | | pH | 7 | 7 | 7 | 7 |
| | | Odour | None | None | None | None |

TABLE 3

| Example | PHMB Conc. on Chemical Pulp (ppm) | Yeast Growth after time (hours) | | | |
|---|---|---|---|---|---|
| | | 0 | 5 | 10 | 15 |
| Control | 0 | $3 \times 10^3$ | $1.5 \times 10^4$ | $3.7 \times 10^5$ | $7 \times 10^6$ |
| 5 | 2000 | $1.2 \times 10^3$ | $3.5 \times 10^3$ | $3 \times 10^3$ | $3 \times 10^4$ |
| 6 | 4000 | $2 \times 10^2$ | $1.7 \times 10^3$ | $3.4 \times 10^3$ | $6.8 \times 10^3$ |

We claim:

1. A composition comprising
   a) a non-woven material containing a mixture of polymeric biguanides subject to desorbtion when the non-woven material is wetted by urine; and
   b) an anionic polymer which is substantially insoluble in urine, said anionic polymer functioning to retain said biguanides on said material when contacted by urine.

2. A composition as claimed in claim 1 wherein the non-woven material is cellulose.

3. A composition as claimed in claim 2 wherein the cellulose is a chemical wood pulp.

4. A composition as claimed in claim 1 wherein the mixture of polymeric biguanides is a mixture of poly (hexamethylene biguanides) of formula (2)

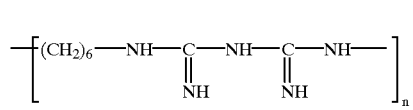

(2)

wherein n is from 2 to 40.

5. A composition as claimed in claim 1 wherein the anionic polymer is substantially insoluble in urine.

6. A composition as claimed in claim 1 wherein the anionic polymer contains carboxylic acid groups.

7. A composition as claimed in claim 1 where the anionic polymer is polyacrylic acid or a copolymer of acrylic acid with one or more non-ionic monomers.

8. A composition as claimed in claim 1 wherein at least some of the anionic groups of the anionic polymer are in free-acid form.

9. A composition as claimed in claim 1 wherein the anionic polymer is a super absorbent.

10. A process for forming an absorbent layer for use in a disposable article which comprises adding an anionic polymer to non-woven fibres containing a mixture of polymeric biguanides which are subject to desorbtion by urine, the anionic polymer being substantially insoluble in urine and functioning to retain the mixture of polymeric biguanides on said fibres.

11. A disposable article containing a composition as claimed in claim 1.

12. A composition according to claim 1 wherein the anionic polymer has a solubility in urine of not greater than 2% by weight.

13. A method of reducing the loss of antimicrobial biguanide bound to a non-woven material on exposure to urine which comprises adding to said non-woven material an anionic polymer which is substantially insoluble in urine.

* * * * *